United States Patent [19]

Schrider et al.

[11] 3,968,207

[45] July 6, 1976

[54] METHOD OF CONTROLLING FLEAS AND TICKS ON CATS AND DOGS

[75] Inventors: Michael Stanley Schrider, South Bound Brook; Gordon Paul Poeschel, Kinnelon, both of N.J.; Anthony Morris Annand, St. Ives, Australia

[73] Assignee: American Cyanamid Company, Stamford, Conn.

[22] Filed: Jan. 23, 1975

[21] Appl. No.: 543,381

Related U.S. Application Data

[63] Continuation-in-part of Ser. No. 423,623, Dec. 10, 1973, abandoned.

[52] U.S. Cl. .............................................. 424/205
[51] Int. Cl.$^2$......................................... A61K 31/66

[58] Field of Search ................................. 424/205

[56] References Cited
OTHER PUBLICATIONS

Abate—Chem. Abst. vol. 76 (1972), p. 21911g.
Steinberg et al. — Chem. Abst. vol. 77, (1972), p. 57566h.

*Primary Examiner*—Sam Rosen
*Attorney, Agent, or Firm*—Denis A. Polyn

[57] ABSTRACT

This invention relates to the use of O,O,O',O'-tetramethyl O,O'-thiodi-p-phenylene phosphorothioate insecticidal and acaricidal compositions in cats and dogs.

13 Claims, No Drawings

METHOD OF CONTROLLING FLEAS AND TICKS ON CATS AND DOGS

This application is a continuation-in-part of our application Ser. No. 423,623, filed Dec. 10, 1973, now abandoned.

SUMMARY OF THE INVENTION

This invention relates to the use of O,O,O',O'-tetramethyl O,O'-thiodi-p-phenylene phosphorothioate insecticidal and acaricidal compositions, in particular as a pesticide to control ticks and fleas on cats and dogs.

The active component of the present invention can be illustrated by the following structure:

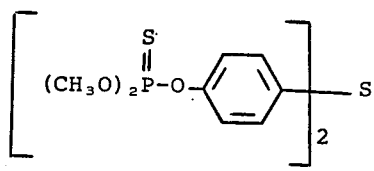

The compound O,O,O',O'-tetramethyl O,O'-thiodi-p-phenylene phosphorothioate may be prepared by reacting the diphenol:

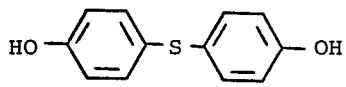

with at least 2 moles of O,O-dimethyl phosphorohalidothioate represented by the formula:

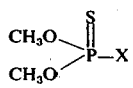

wherein X is halogen, preferably chlorine.

The reaction between the diphenol and the O,O-dimethyl phosphorohalidothioate is carried out on a relative mole basis of one mole of the diphenol to at least 2 moles of the phosphorohalidothioate, although up to 4 moles of the phosphorohalidothioate may be employed to advantage, under alkaline conditions and in the presence of a polar solvent such as water, methyl ethyl ketone, and the like, at a temperature of from between 0° and 100°C. This compound may also be prepared in solvents having a wide range of polarity employing a variety of methods to prevent the accumulation of hydrogen halide by-product. The preparation of the above compound is described in U.S. Pat. Nos. 3,317,636; 3,390,209 and 3,459,856.

We have found that the compound O,O,O',O'-tetramethyl O,O'-thiodi-p-phenylene phosphorothioate is highly effective topically and systemically in controlling fleas and ticks.

The use of O,O,O',O'-tetramethyl O,O'-thiodi-p-phenylene phosphorothioate to control the infestation or reinfestation of dogs and cats by fleas and ticks is a novel use of this material. The use of the aforementioned compound to control insect pests, particularly fleas and ticks on dogs and cats is novel.

It is known that O,O-diethyl O-(2-isopropyl-6-methyl-4-pyrimidinyl)phosphotothiate (Diazinon) and O,O-dimethyl S-(1,2-dicarbethoxyethyl)dithiophosphate (Malathion) are among the insecticides currently used as sprays to control lice on cattle, but it is usually recommended that two applications of these materials be made within a few weeks of each other. The use of O,O-diethyl O-(3,5,6-trichloro-2-pyridyl)phosphorothioate (Dursban chloropyrifos) has been reported by Buchanan et al., New Zealand Vet. Journal 19 (9): 197–202 (1971), to give effective control of lice on cattle with a single spray treatment.

The control of infestations of fleas and ticks or reinfestations of the same, is most desirable because of the economic loses caused by these pests.

Typically, such insects include fleas (Siphonaptera) such as Ctenocephalides felis on dogs and cats.

Among the ectoparasites are included acarina such as Boophilus, Amblyomma, Anocentor, Dermacentor, Ixodes, Haemaphysalis, Hyalomma, Rhipicentor, Morgaropus, Rhipicephalus, Argas, Otobius and Ornithodoros, in the larval, nymph and adult stages, and the method of this invention is particularly useful to control dog fleas (Ctenocephalides canis) and cat fleas (Ctenocephalides felis).

The use of O,O,O',O'-tetramethyl O,O'-thiodi-p-phenylene phosphorothioate to control infestations of fleas on dogs and cats would be particularly advantageous because it is substantially non-toxic at concentrations many times that of the actual amounts employed. The active ingredient, O,O,O',O'-tetramethyl O,O'-thiodi-p-phenylene phosphorothioate, may be conveniently formulated as dusts, dust concentrates, wettable powders, emulsifiable concentrates, and as solutions, with conventional solid or liquid adjuvants. It may also be incorporated in feed or in an animal treat which is highly palatable to the animal. Wettable powders and emulsifiable concentrates are particularly useful since they can be diluted with water and applied topically as dilute liquid sprays to the animals which are to be protected from attack. In the latter situation, the dilute liquid formations may also be used as dips as well as sprays.

Dusts or dust concentrates can be prepared by grinding together the inert solid diluent such as attapulgite, kaolin, walnut shell flour, diatomaceous earth, ground corn cob grits, or ground coconut shell, and the active ingredient, where such active ingredient is in solid form. Where the active ingredient is liquid, it may be sprayed on the carrier and thoroughly mixed with it or it may be dissolved in a solvent such as acetone, xylene, lard or vegetable oils and the solution sprayed on the solid carrier. Dusts usually contain from about 1 to 15% by weight of active ingredient, whereas concentrates may contain from about 16 to about 85% by weight of the active material.

Solutions in organic solvents such as various ketones, lower monohydric aliphatic alcohols, ketoalcohols such as diacetone alcohol, various esters, aromatic and aliphatic hydrocarbons may be applied as a spray or pour-on.

Wettable powders are prepared in the same fashion as dust concentrates, except that about 5 to 10% by weight of a surfactant, and 5 to 10% of a dispersing agent are included therein.

The active component of the present invention may also be prepared as emulsifiable concentrates by dissolving or dispersing about 10 to 75% by weight of the active compound in a suitable solvent or carrier such as a petroleum distillate having a minimum aromatic content of 85% and admixing therewith about 10% by weight of an emulsifier such as polyoxyethylene derivatives and blends with alkyl aryl sulfonates. These concentrates are also generally dispersed in water or other suitable solvent for application.

The application is preferably made at a dose concentration which is lethal for adult insects and acarina, and provides ultimate control of said pests through ovicidal or larvicidal activity.

Application of the active ingredient can be made either directly, as by dusting, dipping and spraying, or by pour-on, or from pressure spray cans.

Application to dogs and cats to control fleas can be effected by spraying each animal with 20 cc. of aqueous solutions containing from 0.0375 to 0.355% (w/v) [0.355% (w/v) contains 0.355 gram of active ingredient per 100 grams of solution] to provide from 1.25 milligrams to 10 milligrams of active material per kilogram of body weight.

Application to dogs and cats to control fleas can also be effected by treating each animal with a dust containing about 2% active ingredient to provide from 10 milligrams to 120 milligrams of active ingredient per kilogram of body weight.

As an ovicidal agent, an application of about 0.1 mg. to 140 mg./kg. of the active ingredient is effective for preventing embryogenesis of insect and acarina ova. Preferably, the rate of application should be from 1 to 100 mg./kg.

As a larvicidal agent, we have found that generally about 0.001 to 1.0% of the compound, O,O,O',O'-tetramethyl O,O'-thiodi-p-phenylene phosphorothioate, is effective for controlling Boophilus microplus larvae. Preferably, the rate of application to larvae ranges from about 0.001 to 0.4%.

The compound O,O,O',O'-tetramethyl O,O'-thiodi-p-phenylene phosphorothioate can be administered to dogs and cats in from 0.5 to 400 mg./kg. of body weight in a physiologically acceptable diluent, including cat and dog food, gelatin and the like.

For systemic control of fleas on cats and dogs, the active ingredient can be incorporated in the animal feed in sufficient amount to provide about 25 ppm to 1000 ppm and preferably 75 ppm to 300 ppm of said ingredient in the feed. This can be accomplished by dispersing the active ingredient in a vegetable oil or fat and spraying this prepared mixture on an edible feed meal such as soybean meal.

In practice, the feed containing the anti flea compound should provide the animal with from 3 to 50 mg./kg./day of said compound for long term feeding, for example, for from several weeks to several months or continuously. Diets providing from 50 to 400 mg./kg./day will generally be administered for periods of short duration, i.e., 1 to 10 days. Weights given as mg./kg./day means mg./kg. of animal body weight per day.

It is of course obvious that the active compound may also be administered orally in the form of a pill, tablet, capsule or oral liquid using traditional carriers and excipients. Dosages should provide the mg./kg./day requirements given above with respect to administration in the feed.

SPECIFIC DISCLOSURE

The present invention is illustrated by the following examples. All parts and percentages are by weight unless otherwise specifically designated.

EXAMPLE 1

Preparation of O,O,O',O'-tetramethyl O,O'-thiodi-p-phenylene phosphorothioate

This compound is prepared by reacting 11 grams (0.05 mole) of 4,4'-thiodiphenol and 5.5 grams (0.1 mole) of sodium methoxide slurried in 400 ml. of methyl ethyl ketone and refluxing for 15 minutes, distilling to remove methanol, diluting with 100 ml. of methyl ethyl ketone and adding 16.2 grams (0.11 mole) of O,O-dimethyl phosphorochloridothioate dissolved in 50 ml of methyl ethyl ketone over 5 minutes under reflux. The mixture is then refluxed for 1.5 hours.

The solids are filtered and the solvent removed under reduced pressure. The residue is dissolved in chloroform and the solution washed with 5% sodium hydroxide, 5% hydrochloric acid, water and saturated sodium chloride solution. The washed solution is then dried and concentrated under reduced pressure to give 18.3 grams of oil. Purification by washing with hexane and chromatography on acid-washed alumina gives pure material $n_D^{25} = 1.5880$.

EXAMPLE 2

Effective control of Siphonaptera is demonstrated by using mongrel dogs experimentally infested with 100 adult Ctenocephalides felis. Dogs used in testing were placed in raised cages with steel grate floors. Three days prior to treatment, 100 fleas were placed on each dog. On the day of treatment each cage was lined with absorbent brown paper. Dogs were treated at various dose levels (1–60 mg./kg.) applied topically using a 2% active ingredient dust formulation, or a dilute aqueous dispersion applied as a spray. Activity was determined by the number of dead fleas recovered from the brown paper, and a systematic examination of the test animal in relation to infested, untreated control dogs.

Residual activity of the initial application of the test compound was done by experimentally reinfesting each dog at 7-day intervals with an additional 100 adult C. felis. Activity was determined as described above. The results obtained are described in Table I.

TABLE I

| | | Activity Against Ctenocephalides on Dogs | | | | | | | |
| Compound | Number of Host Animals Tested | Method of Application | Dose Rate mg/kg | 0 | 7 | Percent Activity 14 | 21 | 25 | 28 | 42 |
| --- | --- | --- | --- | --- | --- | --- | --- | --- | --- | --- |
| 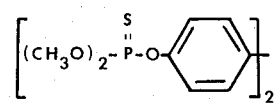 | 1 | Spray (20 cc at 0.355% w/v | 10.0 | 100 | 100 | 100 | 100 | — | 10 | — |
| | 1 | Spray (20 cc at 0.0785% w/v | 2.5 | 100 | 100 | 100 | 0 | — | — | — |
| | 1 | Spray | 1.25 | 100 | 100 | 100 | 100 | 0 | — | — |

TABLE I-continued

| Compound | Number of Host Animals Tested | Activity Against Ctenocephalides on Dogs Method of Application | Dose Rate mg/kg | 0 | 7 | Percent Activity 14 | 21 | 25 | 28 | 42 |
|---|---|---|---|---|---|---|---|---|---|---|
| | | (20 cc at 0.0375% w/v | | | | | | | | |
| | 5 | 2% Dust Form | 40.0 | 100 | 100 | 100 | 100 | — | 100 | 0 |
| | 5 | 2% Dust Form | 20.0 | 100 | 100 | 100 | 100 | — | 100 | 0 |
| | 5 | 2% Dust Form | 10.0 | 100 | 100 | 100 | 100 | — | 80 | 0 |

EXAMPLE 3

Effective control of acarina larvae is demonstrated with *Boophilus microplus* larvae. Boophilus is a one-host tick which uses only one host animal during its three parasitic life stages (larvae, nymph, adult). Varying amounts of a 50% emulsifiable concentrate (technical material 49.6%, MAL 77-L Emulsifier 8.8%, Panasol AN-2 41.6%) of O,O,O',O'-tetramethyl O,O'-thiodi-p-phenylene phosphorothioate is added to water to form a mixture of 0.0001 to 0.10% (w/w). Twenty larvae are enclosed in a pipette sealed at one end with a gauze material, and the "solution" containing the test compound is then drawn through the pipette with a vacuum hose, simulating a spray system. The open end of the pipette is sealed with plastiline and the ticks held for 48 hours at room temperature and 80+% humidity. Activity is based on mortality. The test compound was 100%, 100% and 0% active at 0.01%, 0.001% and 0.0001% (w/w), respectively.

EXAMPLE 4

Effective control of acarina adults is demonstrated with rabbits experimentally infested with adult *Amblyoma americanum* (five males and five females per rabbit). The midsection of each host rabbit is clipped, and a rubber capsule is cemented to the clipped portion of the skin. After a 24-hour drying period, the 10 ticks are placed in the capsule and allowed to attack the host for 72 hours. On the day of treatment, each capsule is sprayed with 2–3 cc. of the test compound, O,O,O',O'-tetramethyl O,O'-thiodi-p-phenylene phosphorothioate. Sufficient rabbits were used to test at concentrations of 0.05%, 0.20% and 0.40% (w/w), respectively.

Mortality was noted 4 days after treatment. On those rabbits where female ticks survived, five untreated male ticks were introduced and the ticks allowed to mate. Fully engorged females were then removed from the capsule and placed in petri dishes for oviposition. Effect of fecundity is then determined by comparing the percent of eggs laid and the percent of eggs which hatch in the treated versus the controls. The results are reported in Table II.

TABLE II

| Control of Ticks (*Amblyomma americanum*) on Rabbits | | | |
|---|---|---|---|
| Treatment Conc. % (w/w) | Deaths (%) Males | Females | Eggs Hatched (%) |
| 0.05 | 70 | 10 | 90 |
| 0.20 | 100 | 40 | 50 |
| 0.40 | 100 | 50 | 1 |

The above results show that application of O,O,O',O'-tetramethyl O,O'-thiodi-p-phenylene phosphorothioate at 0.20% and 0.40% (w/w) effectively controls amblyomma ticks by killing the adult males and some females and rendering the female ova non-viable.

EXAMPLE 5

Five groups of two mongrel dogs each were dosed daily with 0, 0.78, 3.1, 12.5 or 50 mg. O,O,O',O'-tetramethyl O,O'-thiodi-p-phenylene phosphorothioate/kg. body weight in gelatin capsules for 10 days. Medication began three days after infestations with 100 adult *Ctenocephalides felis*. At 50 mg./kg. complete flea control was observed after 24 hours. At 12.5 mg./kg. complete control was observed in one dog after 24 hours and in another dog after 7 days of medication. At 3.1 mg./kg both dogs had complete control after 7 days. At 0.78 mg./kg., no flea activity was observed. Purina High Protein Dog Meal was fed once daily for the duration of the experiment. Water was provided ad libitum. The following table summarizes the results of the test.

Table III

Flea Control On Dogs Given Oral Doses of O,O,O',O'-tetramethyl O,O'-thiodi-p-phenylene phosphorothioate

| Dog No. | Dose (mg/kg.) | Flea Control On Days After Treatment | | | | | | | | |
|---|---|---|---|---|---|---|---|---|---|---|
| | | 0 | 1 | 2 | 3 | 4 | 5 | 6 | 7 | 8 |
| 1 | 50 | NC | 100 | | | | | | | |
| 2 | 50 | NC | 100 | | | | | | | |
| 3 | 12.5 | NC | NC | PC | PC | PC | | | 100 | |
| 4 | 12.5 | NC | 100 | | | | | | | |
| 5 | 3.1 | NC | NC | NC | PC | PC | | | 100 | |
| 6 | 3.1 | NC | NC | NC | PC | PC | | | 100 | |
| 7 | .78 | NC | NC | NC | NC | NC | | | NC | NC |
| 8 | .78 | NC | NC | NC | NC | NC | | | NC | NC |
| 9 | 0.0 | NC | NC | NC | NC | NC | | | NC | NC |
| 10 | 0.0 | NC | NC | NC | NC | NC | | | NC | NC |

Legend:-
100 - 100% Control
PC - Partial Control
NC - No Control

EXAMPLE 6

Five groups of two mongrel dogs each were fed a daily dose of 0, 6.25, 25, 100 or 400 mg. O,O,O',O'-tetramethyl O,O'-thiodi-p-phenylene phosphorothioate/kg. body weight in Agway Big Red Dog Meal.

Dogs eating less than 75% of the food were given a corrected dose by gelatin capsule to equal 100%. Medication began 1 day after infesting each dog with 100 adult Ctenocephalides felis and 2 days before infesting each dog with 10 Dermacentor variabiles and 10 Rhipicephalus sanguineus adults.

Complete flea control was observed after 48 hours on all dogs treated at 400, 100 or 25 mg. of drug/kg. body weight. At 6.25 mg./kg. complete flea control was observed on 1 dog after 3 days and the other dog after 4 days. Both control dogs had fleas after 10 days.

Adult Dermacentor and Rhipicephalus ticks contained in capsules on the body of the 400 mg./kg. dogs were either dead or moribund at the end of the experiment (8 days). Two female Rhipicephalus ticks on the ear of one dog appeared normal, though not completely engorged, at the end of the experiment.

At 100 mg./kg. some of the Dermacentor ticks on one dog appear discolored and stunted but the Rhipicephalus ticks engorged and detached normally.

Both 25 and 6.25 mg./kg. appear ineffective against adults of both dog ticks. The following Table IV summarizes flea control and Table V the tick control under the conditions of the experiment.

Table IV

| Dog No. | Dose (mg/kg.) | Flea Control on Dogs After Treatment | | | | | | | | |
|---|---|---|---|---|---|---|---|---|---|---|
| | | 0 | 1 | 2 | 3 | 4 | 5 | 6 | 7 | 8 |
| 1 | 400 | | | 100 | | | | | | |
| 2 | 400 | | | 100 | | | | | | |
| 3 | 100 | | | 100 | | | | | | |
| 4 | 100 | | | 100 | | | | | | |
| 5 | 25 | | | 100 | | | | | | |
| 6 | 25 | | | 100 | | | | | | |
| 7 | 6.25 | | | NC | PC | 100 | | | | |
| 8 | 6.25 | | | PC | 100 | | | | | |
| 9 | 0 | | | NC | NC | NC | NC | NC | NC | NC |
| 10 | 0 | | | NC | NC | NC | NC | NC | NC | NC |

Legend:
100 - 100% Control
PC - Partial Control
NC - No Control

TABLE V

Tick Mortality on Dogs Fed a Diet Containing O,O,O′,O′-tetramethyl O,O′-thiodi-p-phenylene phosphorothioate

| Dose (mg./kg.) | % R.S. | Control of Adult Engorged Female Ticks D.V. |
|---|---|---|
| 400 | 100 | 100 |
| 100 | 50 | 30 |

TABLE V-continued

Tick Mortality on Dogs Fed a Diet Containing O,O,O′,O′-tetramethyl O,O′-thiodi-p-phenylene phosphorothioate

| Dose (mg./kg.) | % R.S. | Control of Adult Engorged Female Ticks D.V. |
|---|---|---|
| 25 | 0 | 10 |
| 6.25 | 20 | 0 |
| 0.20 | 0 | |

Legend:
R.S. - Rhipicephalus sanguineus
D.V. - Dermacentor variabilis

EXAMPLE 7

An experiment was conducted using O,O,O′,O′-tetramethyl O,O′-thiodi-p-phenylene phosphorothioate which was prepared from a 25% concentrate diluted with talc so the final powder was 2% drug. Prior to the start of the test 23 cats were classified according to sex, age, hair length and color and divided into five groups. One of these groups was then randomly selected to be the controls and the other groups were assigned for treatment in a random order. The amount of 2% drug dust applied to each cat was calculated prior to treatment to give a dose rate of 60 mg. drug/kg. The duster was weighed before treating each cat and at intervals during dusting to get as near the desired dose as possible. Table VI hereinafter shows the weight of cats used in the experiment along with the amount of drug used. Table VII summarizes the results obtained up to 48 days after treatment.

TABLE VI

2 % O,O,O′,O′-Tetramethyl O,O′-thiodi-p-phenylene phosphorothioate Powder Against Experimental Infestations of Ctenocephalides felis on Cats

| Cat No. | Weight (kg.) | Grams of Powder Applied | Actual Dose (mg./kg.) |
|---|---|---|---|
| 218 | 2.12 | 6 | 0 |
| 199 | 3.72 | 14 | 0 |
| 208 | 3.52 | 7 | 0 |
| 191 | 2.88 | 9 | 0 |
| 202 | 1.76 | 5 | 56.8 |
| 188 | 3.20 | 10 | 62.5 |
| 205 | 2.80 | 8 | 57.1 |
| 197 | 3.04 | 10 | 65.8 |
| 203 | 3.56 | 11 | 61.8 |
| 210 | 2.00 | 6 | 60.0 |
| 207 | 3.74 | 13 | 69.5 |
| 206 | 3.18 | 10 | 62.9 |
| 173 | 3.46 | 7 | 40.5 |
| 194 | 2.38 | 7 | 58.8 |
| 204 | 4.30 | 19 | 88.4 |
| 212 | 2.72 | 8 | 58.8 |
| 196 | 3.48 | 6 | 34.5 |
| 201 | 2.94 | 7 | 47.6 |
| 209 | 2.52 | 8 | 63.5 |
| 192 | 4.50 | 13.5 | 60.0 |
| 215 | 3.52 | 10.5 | 59.7 |

TABLE VI-continued

2 % O,O,O',O'-Tetramethyl O,O'-thiodi-p-phenylene phosphorothioate Powder Against Experimental Infestations of Ctenocephalides felis on Cats

| Cat No. | Weight (kg.) | Grams of Powder Applied | Actual Dose (mg./kg.) |
|---|---|---|---|
| 195 | 3.72 | 12 | 64.5 |
| 92 | 3.34 | 10 | 59.9 |
| Average for Treated Cats | | | 59.7 |

TABLE VII

Flea Counts on Cats Dusted with 2% O,O,O',O'-Tetramethyl O,O'-thiodi-p-phenylene phosphorothioate Powder
Flea Counts - Days After Treatment*

| Cat. No. | 1 | 2 | 8 | 9 | 15 | 16 | 17 | 22 | 26 | 27 | 29 | 30 | 33 | 34 | 36 | 37 | 40 | 41 | 43 | 44 | 47 | 48 |
|---|---|---|---|---|---|---|---|---|---|---|---|---|---|---|---|---|---|---|---|---|---|---|
| Controls (4 cats) | + | + | + | + | + | + | + | + | + | + | + | + | + | + | + | + | + | + | + | + | + | + |
| 202 | − | − | − | − | + | − | − | + | + | + | + | + | + | + | | | | | | | | |
| 188 | − | − | − | − | − | − | − | − | + | + | − | − | + | − | − | | + | + | + | − | | |
| 205 | − | − | − | − | + | − | − | + | + | + | + | + | + | + | | | | | | | | |
| 197 | − | − | − | − | − | − | + | − | + | + | + | − | + | + | + | + | | | | | | |
| 203 | − | − | − | − | − | − | − | − | + | − | − | | | | − | − | | | − | − | − | |
| 210 | − | − | − | − | − | − | + | − | + | + | + | + | | | | | | | | | | |
| 207 | − | − | − | − | − | − | − | − | − | − | | | + | + | + | − | + | + | + | + | | |
| 206 | − | − | − | − | − | − | + | − | + | + | − | − | + | + | + | + | | | | | | |
| 173 | − | − | − | − | − | − | − | − | + | − | − | + | | | | | | | | | | |
| 194 | − | − | − | − | + | − | − | + | − | | + | + | + | + | | | | | | | | |
| 204 | − | − | − | − | − | − | − | − | − | − | | | − | − | | | | | − | − | − | |
| 212 | − | − | − | − | − | − | − | − | + | − | + | − | + | + | + | + | | | | | | |
| 196 | − | − | − | − | − | − | + | − | − | + | + | + | + | | | | | | | | | |
| 201 | − | − | − | − | − | − | − | − | + | + | + | + | | | | | | | | | | |
| 209 | − | − | − | − | − | − | − | − | + | − | − | | + | + | + | − | + | + | + | + | | |
| 192 | − | − | − | − | − | − | − | − | − | − | | | − | − | | | | | + | + | + | − |
| 215 | − | − | − | − | − | − | − | − | + | + | − | − | + | + | + | + | | | | | | |
| 195 | − | − | − | − | − | − | − | − | − | − | | | − | − | | | | | − | − | − | |
| 92 | − | − | − | − | − | − | + | − | − | − | | | | | − | + | − | + | | | | |

Notes:
− = No fleas or only dead fleas found
+ = Live fleas found
No entry-cat was not examined
*Cats initially infested with 100 C. felis on day -2 then reinfested on days 7, 14, 21, 28, 35, 42

The above results show excellent residual control against *C. felis* on cats was obtained for four weeks. The use of 60 mg. of O,O,O',O'-tetramethyl O,O'-thiodi-p-phenylene phosphorothioate per kilogram in the form of a 2% powder produced 100% control for three weeks; 90% the fourth week; 64% the fifth week and 40% the sixth week.

EXAMPLE 8

An experiment was carried out using 2% O,O,O',O'-tetramethyl O,O'-thiodi-p-phenylene phosphorothioate pressurized spray having the following formula

| | Percent |
|---|---|
| O,O,O',O'-tetramethyl O,O'-thiodi-p-phenylene phosphorothioate | 2.2 |
| PEG | 2.5 |
| Isopropyl Alcohol | 42.4 |
| Genetron 11 | 33.8 |
| Genetron 12 | 18.8 |
| Masking Agent (BQTV 1480) | 0.3 |

Mongrel cats were obtained from a laboratory animal dealer. On arrival cats were caged singly, fed one cup of Purina Cat Chow daily and given chlortetracycline medicated drinking water ad libitum. Four cats, numbers 91, 93, 100 and 101 were from litters that had been raised in our own laboratories. The cats were held at least 3 weeks prior to the start of a test to insure that they were in good health. Two separate rooms were used to house the cats and a proportionate number of test and control cats were held in each room during the two trials. Prior to the start of each trial the cats were classified according to sex, age, hair length and color and divided into five similar groups of five cats each. One of these groups was then randomly selected to be the controls and the other groups were assigned for treatment in a random order. The amount of 2% drug spray applied to each cat from a pressure can was calculated prior to treatment to give a dose rate of 60 mg. actual drug per kg. of animal body weight. The spray can was weighed before spraying each cat and then weighed at intervals during spraying to come as close to the desired dose as possible. During dosing an attempt was made to distribute the spray evenly over the entire surface area of the cat. The cats were removed from their cage and examined for live fleas by two technicians. As soon as a live flea was found the examination was terminated. Any dead fleas found in the fur were removed and counted. Only cats which were clear of fleas 34 days after treatment and controls were reinfested on day 35. Activity in both trials was based on absence or presence of fleas and not on percent reduction of flea populations. Percent activity figures used in Table VIII hereinafter were calculated using the following formula:

$$\frac{\text{Number of cats free of fleas}}{\text{Total Number of cats tested}} \times 100 = \text{percent control}$$

Tables VIII and IX hereinafter summarize the weight of cats, grams spray, and actual dose of drug in trials 1 and 2. Flea Counts on days after treatment for trials 1 and 2 are given in Tables X and XI, respectively.

TABLE VIII

2% O,O,O1',O'-Tetramethyl O,O'-Thiodi-p-Phenylene Phosphorothioate Pressurized Spray Against Ctenocephalides felis Infestations in Cats (Trial 1)

| Cat. No. | Weight (kg.) | Grams Spray Applied | Actual Drug Dose (mg./kg.) |
|---|---|---|---|
| 3 | 3.15 | 11.0 | 0 |
| 0 | 3.9 | 8.0 | 0 |
| 2 | 2.2 | 7.0 | 0 |
| 8 | 3.35 | 10.0 | 0 |
| 0 | 2.75 | 8.0 | 0 |
| 128 | 3.3 | 10.0 | 60.6 |
| 91 | 3.15 | 8.5 | 53.96 |
| 151 | 1.9 | 7.0 | 73.68 |
| 117 | 3.45 | 11.0 | 63.76 |
| 83 | 3.5 | 11.5 | 65.71 |
| 161 | 3.1 | 10.0 | 64.51 |
| 159 | 2.4 | 7.5 | 62.5 |
| 154 | 2.2 | 6.5 | 59.09 |
| 140 | 3.4 | 11.0 | 64.7 |
| 157 | 2.0 | 7.5 | 75.0 |
| 93 | 1.35 | 4.0 | 59.25 |
| 119 | 5.55 | 17.0 | 61.26 |
| 155 | 2.25 | 7.0 | 62.22 |
| 146 | 3.0 | 9.5 | 63.33 |
| 150 | 1.75 | 6.0 | 68.57 |
| 73 | 2.9 | 8.5 | 58.62 |
| 101 | 3.75 | 12.0 | 64.0 |
| 147 | 1.75 | 6.0 | 68.57 |
| 124 | 3.5 | 11.0 | 62.85 |
| 153 | 2.3 | 7.0 | 60.86 |
| Average for treated cats | | | 63.54 |

TABLE IX

2% O,O,O',O'-Tetramethyl O,O'-Thiodi-p-Phenylene Phosphorothioate Pressurized Spray Against Ctenocephalides felis Infestations in Cats (Trial 2)

| Cat. No. | Weight (kg.) | Grams Spray Applied | Actual Drug Dose (mg./kg.) |
|---|---|---|---|
| 188 | 2.5 | 8.0 | 0 |
| 169 | 2.9 | 12.0 | 0 |
| 173 | 3.0 | 9.0 | 0 |
| 179 | 3.2 | 10.0 | 0 |
| 185 | 4.5 | 14.0 | 0 |
| 194 | 2.7 | 9.5 | 0 |
| 166 | 2.9 | 9.0 | 62.07 |
| 143 | 2.9 | 8.5 | 58.62 |
| 183 | 4.0 | 13.0 | 65.0 |
| 156 | 2.2 | 7.0 | 63.64 |
| 186 | 2.9 | 10.0 | 68.97 |
| 167 | 2.5 | 7.5 | 60.0 |
| 171 | 3.1 | 9.5 | 61.29 |
| 130 | 4.1 | 12.5 | 60.98 |
| 174 | 3.2 | 9.5 | 59.38 |
| 187 | 3.1 | 9.0 | 58.06 |
| 168 | 2.3 | 7.0 | 60.87 |
| 189 | 3.2 | 10.5 | 65.63 |
| 178 | 3.3 | 9.5 | 57.58 |
| 100 | 3.2 | 9.5 | 59.38 |
| 181 | 3.5 | 11.5 | 65.71 |
| 170 | 2.3 | 7.0 | 60.87 |
| 175 | 4.6 | 13.5 | 58.70 |
| 180 | 3.2 | 9.5 | 59.38 |
| 176 | 3.1 | 9.0 | 58.06 |
| 190 | 3.2 | 10.0 | 62.5 |
| Average for treated cats | | | 61.33 |

TABLE X

Flea Counts on Cats Sprayed with 2% O,O,O',O'-Tetramethyl O,O'-thiodi-p-phenylene phosphorothioate Pressurized Spray (Trial 1) Flea Counts - Days After Treatment*

| Cat No. | 1 | 2 | 5 | 8 | 9 | 15 | 16 | 22 | 23 | 26 | 27 | 29 | 30 | 33 | 34 | 36 | 37 | 40 | 41 |
|---|---|---|---|---|---|---|---|---|---|---|---|---|---|---|---|---|---|---|---|
| Control (5 cats) | + | + | + | + | + | + | + | + | + | + | + | + | + | + | + | + | + | + | + |
| 128 | − | − | − | − | − | − | − | + | + | + | + | + | + | + | + | | | | |
| 91 | − | − | − | − | − | − | − | + | − | − | | | + | − | − | | − | − | + − |
| 151 | − | − | | − | − | − | − | + | + | − | + | + | + | + | + | | | | |
| 117 | − | − | | − | − | − | − | + | − | − | | | + | + | + | + | | | |
| 83 | − | − | | − | − | − | − | − | − | − | | | | | | + | − | − | |
| 161 | − | − | | − | − | − | − | + | + | − | − | | + | + | − | − | + | + | + |
| 159 | − | − | | − | − | − | − | + | + | − | − | | + | + | + | + | | | |
| 154 | − | − | | − | − | − | − | + | − | + | − | | + | + | + | + | | | |
| 140 | − | − | | − | − | − | − | + | + | + | + | | + | + | + | + | | | |
| 157 | − | − | | − | − | − | − | − | + | + | + | | + | + | + | + | | | |
| 93 | − | − | | − | − | − | − | + | − | − | | | + | − | − | | + | − | − − |
| 119 | − | − | | − | − | − | − | + | + | + | + | | + | + | + | + | | | |
| 155 | − | + | | − | − | − | − | − | + | − | − | | | | + | + | + | + | |
| 146 | − | − | | − | − | − | − | + | − | − | | | + | + | − | − | + | + | − − |
| 150 | − | − | | − | − | − | − | + | + | + | + | | + | + | + | + | | | |
| 73 | − | − | | − | − | − | − | − | − | − | | | − | + | − | − | + | − | − − |
| 101 | − | − | | − | + | − | + | − | − | | | | + | + | − | + | + | + | + + |
| 147 | − | − | | − | − | − | − | + | + | − | − | | + | + | + | + | | | |
| 124 | − | − | | − | − | − | − | + | − | − | | | + | + | + | − | + | + | + + |
| 153 | − | − | | − | − | − | − | + | + | + | + | | + | + | + | + | | | |

Notes:
− = No fleas or only dead fleas found
+ = Live fleas found
   No Entry Cat was not examined
*Cats initially infested with 100 C. felis on day -2 then reinfested on days 7, 14, 21, 28, 35.

TABLE XI

Flea Counts on Cats Sprayed with 2% O,O,O',O'-Tetramethyl O,O'-thiodi-p-phenylene phosphorothioate Pressurized Spray (Trial 2) Flea Counts - Days After Treatment*

| Cat No. | 1 | 2 | 8 | 9 | 15 | 16 | 19 | 22 | 23 | 26 | 27 | 29 | 30 | 33 | 34 | 36 | 37 | 41 |
|---|---|---|---|---|---|---|---|---|---|---|---|---|---|---|---|---|---|---|
| Controls (5 cats) | + | + | + | + | + | + | + | + | + | + | + | + | + | + | + | + | + | + |
| Control 169 | + | − | − | − | − | − | − | + | + | − | | + | − | − | | + | − | − |
| 166 | − | − | − | − | − | − | − | | + | − | − | | + | + | − | − | + | + + |
| 143 | − | − | − | − | − | − | − | | + | − | − | | + | + | + | + | | |
| 183 | − | − | − | − | − | − | − | | − | − | | | − | − | | | − | − − |
| 156 | − | − | − | − | − | − | − | | + | − | − | | + | + | + | + | | |
| 186 | − | − | − | − | − | − | − | | + | − | − | | − | − | | | − | − − |
| 167 | − | − | − | − | + | − | − | | + | + | + | | + | + | + | + | | |
| 171 | − | − | − | − | − | − | − | | + | − | − | | + | + | − | + | | |
| 130 | − | − | − | − | − | − | − | | − | − | | | − | − | | | − | − − |
| 174 | − | − | − | − | − | − | − | | − | − | | | − | − | | | − | − − |
| 187 | − | − | − | − | − | − | − | | + | − | − | | + | + | + | + | | |
| 168 | − | − | − | − | − | − | − | | + | − | − | | + | + | + | + | | |
| 189 | − | − | − | − | − | − | − | | + | + | − | | + | + | + | + | | |
| 178 | − | − | − | − | − | − | − | | + | − | − | | + | − | + | − | − | + − |
| 100 | − | − | − | − | − | − | − | | − | − | | | + | − | − | | + | + + |
| 181 | − | − | − | − | − | − | − | | + | − | − | | + | + | − | + | | |
| 170 | − | − | − | − | + | + | − | | + | + | + | | + | + | + | + | | |
| 175 | − | − | − | − | − | − | − | | − | − | | | + | − | − | | + | + + |
| 180 | − | − | − | − | − | − | − | | − | − | | | + | + | − | + | | |
| 176 | − | − | − | − | − | − | − | | + | − | − | | + | + | + | + | | |
| 190 | − | − | − | − | − | − | − | | + | + | + | | + | + | + | + | | |

Notes:
− = No fleas or only dead fleas found
+ = Live fleas found
   No Entry Cat was not examined
*Cats initially infested with 100 C. felis on the day -2 then reinfested on days 7, 14, 21, 28, 35.

EXAMPLE 9

An experiment was carried out to determine the activity of O,O,O',O'-tetramethyl O,O'-thiodi-p-phenylene phosphorothioate 2% powder for the control of *Ctenocephalides felis* infestations on dogs. A group of 40 dogs of mixed breeds were obtained from a licensed laboratory animal dealer and housed in individual cages. The 2% powder was formulated from a 25% dust concentrate containing 26% O,O,O',O'-tetramethyl O,O'-thiodi-p-phenylene phosphorothioate, 24% celite 209 and 50% acidic kaolin. Talc was used to dilute the concentrate to 2% active ingredient. Each dog was infested with 100 1 day old adult *C. felis* 72 hours prior to treatment and reinfested on a weekly basis for 6 weeks beginning 7 days after treatment. Each dog was treated with 20 mg. actual drug per kg. body weight formulated as a 2% powder. Five or more dogs were treated with a blank powder and used as infested controls. Table XII hereinafter summarizes results obtained in two separate tests of 20 dogs each. Tables XIII and XIV summarizes dead fleas obtained from papers placed under each dog cage. Table XV summarizes average dead fleas in treated versus average dead fleas in control.

TABLE XII

Activity of 2% O,O,O',O'-Tetramethyl O,O'-thiodi-p-phenylene phosphorothioate Powder Applied at 20 mg./kg. on Dogs Number of Dogs on Which Fleas Were Controlled

| Experiment | Weeks After Treatment | | | | | | |
|---|---|---|---|---|---|---|---|
| | 0 | 1 | 2 | 3 | 4 | 5 | 6 |
| 1* | 20 | 20 | 20 | 20 | 17 | 14 | 5 |
|  | 20 | 20 | 20 | 20 | 20 | 20 | 20 |
| 2* | 20 | 20 | 20 | 20 | 20 | 18 | 13 |
|  | 20 | 20 | 20 | 20 | 20 | 20 | 20 |
| Combination of | 40 | 40 | 40 | 40 | 37 | 32 | 18 |
| Test 1 & 2 | 40 | 40 | 40 | 40 | 40 | 40 | 40 |
| Percent of Dogs with Control | 100 | 100 | 100 | 100 | 92.5 | 80 | 45 |

*All control dogs remained infested for the duration of the experiments; one exception was noted due to accidental exposure to O,O,O',O'-tetramethyl O,O'-thiodi-p-phenylene phosphorothioate

TABLE XIII

Individual Data on Number of Dead Fleas Recovered (Trial 1)
No. of Dead Fleas Recovered in 48 Hrs.

| Dog | Treatment Dose Rate (mg./kg.) | Weeks After Treatment | | | | | | |
|---|---|---|---|---|---|---|---|---|
| | | 0 | 1 | 2 | 3 | 4 | 5 | 6 |
| 208 | Control | 5 | 11 | 13 | 13 | 2 | 3 | 0 |
| 225 | Control | 0 | 6 | 5 | 7 | 4 | 4 | 0 |
| 228 | Control | 26 | 80* | 1 | 2 | 4 | 3 | 2 |
| 232 | Control | 0 | 5 | 2 | 6 | 10 | 1 | 7 |
| 237 | Control | 0 | 0 | 3 | 6 | 3 | 3 | 7 |
| 17 | 20 | 18 | 30 | 54 | 37 | 43 | 35 | 5 |
| 61 | 20 | 44 | 44 | 39 | 36 | 46 | 63 | 49 |
| 185 | 20 | 41 | 53 | 55 | 47 | 48 | 48 | 63 |
| 195 | 20 | 34 | 43 | 40 | 43 | 25 | 16 | 10 |

TABLE XIII-continued

Individual Data on Number of Dead Fleas Recovered (Trial 1)
No. of Dead Fleas Recovered in 48 Hrs.

| Dog | Treatment Dose Rate (mg./kg.) | Weeks After Treatment | | | | | | |
|---|---|---|---|---|---|---|---|---|
| | | 0 | 1 | 2 | 3 | 4 | 5 | 6 |
| 204 | 20 | 26 | 14 | 27 | 35 | 8 | 5 | 3 |
| 207 | 20 | 38 | 37 | 64 | 42 | 21 | 5 | 1 |
| 210 | 20 | 28 | 26 | 31 | 33 | 35 | 21 | 23 |
| 211 | 20 | 50 | 74 | 44 | 63 | 61 | 48 | 19 |
| 214 | 20 | 21 | 43 | 38 | 44 | 24 | 11 | 3 |
| 220 | 20 | 22 | 49 | 32 | 42 | 34 | 36 | 6 |
| 221 | 20 | 21 | 57 | 43 | 43 | 35 | 36 | 19 |
| 224 | 20 | 40 | 33 | 50 | 60 | 6 | 14 | 7 |
| 226 | 20 | 24 | 31 | 42 | 29 | 26 | 46 | 27 |
| 234 | 20 | 25 | 37 | 44 | 60 | 42 | 39 | 35 |
| 235 | 20 | 28 | 38 | 37 | 35 | 28 | 45 | 30 |
| 236 | 20 | 26 | 19 | 30 | 37 | 32 | 19 | 10 |
| 252 | 20 | 48 | 60 | 44 | 39 | 13 | 5 | 5 |
| 254 | 20 | 29 | 31 | 25 | 50 | 37 | 57 | 27 |
| 255 | 20 | 33 | 30 | 33 | 38 | 32 | 33 | 12 |
| 966 | 20 | 34 | 46 | 37 | 42 | 28 | 10 | 7 |

*Dog No. 228 accidentally exposed to O,O,O',O'-tetramethyl O,O'-thiodi-p-phenylene phosphorothioate

TABLE XIV

Individual Data on No. of Dead Fleas Recovered in 48 Hrs. (Trial 2)

| Dog | Treatment Dose Rate (mg./kg.) | Weeks after Treatment | | | | | | |
|---|---|---|---|---|---|---|---|---|
| | | 0 | 1 | 2 | 3 | 4 | 5 | 6 |
| 266 | Control | 21 | 2 | 0 | 9 | 7 | 1 | 7 |
| 271 | Control | 8 | 0 | 1 | 5 | 6 | 2 | 2 |
| 275 | Control | 3 | 0 | 5 | 7 | 2 | 7 | 2 |
| 276 | Control | 19 | 3 | 3 | 4 | 2 | 2 | 2 |
| 277 | Control | 2 | 1 | 0 | 7 | 8 | 5 | 4 |
| 278 | Control | 18 | 0 | 0 | 6 | 3 | 0 | 5 |
| 262 | 20 | 72 | 48 | 34 | 45 | 35 | 27 | 24 |
| 263 | 20 | 39 | 44 | 36 | 41 | 39 | 21 | 10 |
| 264 | 20 | 54 | 38 | 41 | 38 | 51 | 45 | 16 |
| 265 | 20 | 55 | 48 | 43 | 48 | 34 | 4 | 4 |
| 267 | 20 | 49 | 46 | 49 | 47 | 23 | 2 | 3 |
| 268 | 20 | 78 | 49 | 62 | 42 | 29 | 21 | 20 |
| 269 | 20 | 57 | 28 | 39 | 27 | 35 | 28 | 53 |
| 270 | 20 | 38 | 49 | 30 | 35 | 50 | 30 | 50 |
| 272 | 20 | 42 | 48 | 31 | 44 | 36 | 28 | 7 |
| 273 | 20 | 59 | 74 | 75 | 80 | 50 | 47 | 44 |
| 279 | 20 | 30 | 32 | 35 | 35 | 26 | 11 | 8 |
| 281 | 20 | 48 | 20 | 36 | 28 | 36 | 34 | 18 |
| 282 | 20 | 20 | 55 | 73 | 50 | 7 | 25 | 4 |
| 283 | 20 | 31 | 33 | 55 | 72 | 45 | 52 | 49 |
| 284 | 20 | 25 | 59 | 59 | 37 | 55 | —* | —* |
| 285 | 20 | 68 | 37 | 37 | 44 | 42 | 48 | 35 |
| 286 | 20 | 30 | 39 | 39 | 37 | 32 | 29 | 27 |
| 287 | 20 | 30 | 55 | 37 | 50 | 75 | 50 | 41 |
| 288 | 20 | 35 | 47 | 60 | 55 | 111** | 40 | 35 |
| 289 | 20 | 10 | 39 | 43 | 35 | 73 | 36 | 20 |

*Dog No. 284 was a pregnant bitch that whelped during the 4th week of the experiment. Therefore no "paper" counts were made during the last 2 weeks of the experiment.
**Dog No. 288 was inadvertently infested with more than 100 C. felis.

TABLE XV

| Test | No. of Treated Dogs/ No. of Control Dogs | Dead Fleas Recovered From Papers Placed Under Cages Average Dead in Treated/Average Dead in Control Weeks After Treatment | | | | | | |
|---|---|---|---|---|---|---|---|---|
| | | 0 | 1 | 2 | 3 | 4 | 5 | 6 |
| No. 1 | 20/5 | 31.5/6.2 | 39.8/5.5* | 40.4/4.8 | 42.7/6.8 | 31.2/4.6 | 29.6/2.8 | 18.0/3.2 |
| No. 2 | 20/6 | 43.5/11.8 | 44.4/1.0 | 45.7/1.5 | 44.5/6.3 | 44.2/4.7 | 30.4**/2.8 | 24.6**/3.6 |

*Data on one control dog was omitted because of accidental drug exposure.
**Data omitted on a pregnant bitch that whelped during the 4th week of the trial.

EXAMPLE 10

An experiment was carried out on dogs obtained from a licensed laboratory animal dealer. These dogs were mixed breeds and of different size and sex. The dogs were individually housed in cages with absorbent paper placed under each in order to count dead fleas. A mixture containing 2% O,O,O',O'-tetramethyl O,O'-thiodi-p-phenylene phosphorothioate (active ingredient) and having the following formula was used as a pressurized spray:

| | Percent |
|---|---|
| O,O,O',O'-tetramethyl O,O'-thiodi-p-phenylene phosphorothioate | 2.2 |
| PEG 200 | 2.5 |
| Isopropyl Alcohol | 42.4 |
| Genetron 11 | 33.8 |
| Genetron 12 | 18.8 |
| Masking Agent (BQTV 1480) | 0.3 |

Two tests were carried out, one with 22 dogs and the other with 21 dogs, each test using 5 control dogs. Each dog was treated with approximately 60 mg./kg. of O,O,O',O'-tetramethyl O,O'-thiodi-p-phenylene phosphorothioate using the formulation described above. Each dog was infested with 100 1-day old adult *C. felis* 72 hours prior to spray treatment and reinfested on a weekly basis for 7 weeks, beginning 7 days after treatment. The five control dogs were treated with a blank spray containing everything except the active ingredient. After treatment or each reinfestation, daily examinations of each dog were made up to 7 days or until no live fleas could be found. Once a live flea was found, the dog was considered still infested even though the flea population may have been low. Flea control data expressed as No. of Dogs with control/No. of Dogs Treated are summarized in Table XVI. The number of dead fleas recovered from papers under the cages are expressed as average dead on treated/average dead on control are summarized in Table XVII.

TABLE XVI

Activity of 2% O,O,O',O'-Tetramethyl O,O'-thiodi-p-phenylene phosphorothioate Pressurized Spray Applied at 60 mg. actual/kg. body weight of Dogs Number of Dogs on Which Fleas were Controlled

| Experiment | Weeks after Treatment | | | | | | | |
|---|---|---|---|---|---|---|---|---|
| | 0 | 1 | 2 | 3 | 4 | 5 | 6 | 7 |
| 1* | 22 | 22 | 22 | 22 | 22 | 22 | 20 | 12 |
| | 22 | 22 | 22 | 22 | 22 | 22 | 22** | 21 |
| 2* | 21 | 21 | 21 | 20 | 19 | 18 | 14 | 12 |
| | 21 | 21 | 21 | 20** | 20 | 20 | 20 | 20 |
| Combination of Test 1 & 2 | 43 | 43 | 43 | 42 | 41 | 40 | 34 | 24 |
| | 43 | 43 | 43 | 42 | 42 | 42 | 41 | 41 |
| Percent of Dogs with Control | 100 | 100 | 100 | 100 | 97.6 | 95.2 | 82.9 | 58.5 |

*All control dogs remained infested for the duration of the experiments.
**One dog died from a respiratory infection.

TABLE XVII

Dead Fleas Recovered on Papers Placed Under Cages

| Weeks After Treatment | Avg. Dead on Treated/Avg. Dead on Control | | |
|---|---|---|---|
| | Test 1 | Test 2 | Average on Two Tests |
| 0 | 34.6 | 38.0 | 36.3 |
| | 38 | .2 | 2.0 |
| 1 | 38.2 | 44.5 | 41.4 |
| | 10.4 | .8 | 5.6 |
| 2 | 42.1 | 40.3 | 41.2 |
| | 3.4 | 2.6 | 3.0 |
| 3 | 41.6 | 40.7 | 41.2 |
| | 4.6 | 5.0 | 4.8 |
| 4 | 37.8 | 43.6 | 40.7 |
| | 5.4 | 5.0 | 5.2 |
| 5 | 34.1 | 37.9 | 36.0 |
| | 5.0 | 6.2 | 5.6 |
| 6 | 34.1 | 26.0 | 30.0 |
| | 6.2 | 3.5 | 4.8 |
| 7 | 30.8 | 21.8 | 26.3 |
| | 6.6 | 3.0 | 4.8 |

Each test represents 20 to 22 treated and 4 to 5 control dogs.

The above tests show a 2% pressurized spray is highly active in the control of *Ctenocephalides felis* on dogs.

We claim:

1. A method for controlling fleas and ticks on cats and dogs which comprises administering to said animals a fleaicidal or tickicidal amount of O,O,O',O'-tetramethyl O,O'-thiodi-p-phenylene phosphorothioate.

2. A method according to claim 1, wherein the O,O,O',O'-tetramethyl O,O'-thiodi-p-phenylene phosphorothioate is topically administered with a diluent.

3. A method according to claim 1, wherein the active ingredient is topically administered by spraying.

4. A method according to claim 1, wherein the active ingredient is administered by dipping.

5. A method according to claim 1, wherein the active ingredient is administered by dusting.

6. A method according to claim 1, wherein the active ingredient is orally administered.

7. A method according to claim 1 for the control of fleas on a dog comprising, applying to said dog a flea killing amount of a dilute dispersion containing O,O,O',O'-tetramethyl O,O'-thiodi-p-phenylene phosphorothioate.

8. A method according to claim 1, in which the active ingredient is topically administered to dogs at a level of from 0.1 milligram to 140 milligrams per kilogram of animal body weight.

9. A method according to claim 1 for the control of fleas on cats comprising topically administering to said cats an insecticidal amount of O,O,O',O'-tetramethyl O,O'-thiodi-p-phenylene phosphorothioate.

10. A process for controlling fleas and ticks on cats and dogs characterized by administering from 0.5 to 400 mg. of O,O,O',O'-tetramethyl O,O'-thiodi-p-phenylene phosphorothioate/kg. body weight and a physiologically acceptable diluent for oral administration to said animals.

11. A process according to claim 10 wherein the diluent is a nutritionally balanced diet.

12. A process according to claim 10 wherein the diluent is a gelatin.

13. A process according to claim 10 wherein the diluent is an animal treat.

* * * * *